(12) United States Patent
Nöcker et al.

(10) Patent No.: US 12,357,550 B2
(45) Date of Patent: Jul. 15, 2025

(54) HAIR DYEING COMPOSITION WITH IMPROVED DURABILITY

(71) Applicant: KAO CORPORATION, Tokyo (JP)

(72) Inventors: Bernd Nöcker, Darmstadt (DE); Steven Breakspear, Darmstadt (DE); Fariba Ghiasi, Darmstadt (DE); Niu Jian, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 15 days.

(21) Appl. No.: 18/245,963

(22) PCT Filed: Sep. 20, 2021

(86) PCT No.: PCT/EP2021/075790
§ 371 (c)(1),
(2) Date: Mar. 20, 2023

(87) PCT Pub. No.: WO2022/069279
PCT Pub. Date: Apr. 7, 2022

(65) Prior Publication Data
US 2023/0381078 A1    Nov. 30, 2023

(30) Foreign Application Priority Data
Sep. 30, 2020    (EP) .................................... 20199263

(51) Int. Cl.
*A61Q 5/10* (2006.01)
*A61K 8/41* (2006.01)
*A61Q 5/06* (2006.01)

(52) U.S. Cl.
CPC .............. *A61K 8/416* (2013.01); *A61Q 5/065* (2013.01); *A61K 2800/4322* (2013.01)

(58) Field of Classification Search
CPC ............ A61K 8/416; A61K 2800/4322; A61K 2800/432; A61K 2800/884; A61K 8/411; A61K 8/418; A61Q 5/065
USPC .......................................................... 8/405
See application file for complete search history.

(56) References Cited

U.S. PATENT DOCUMENTS

| | | |
|---|---|---|
| 7,078,498 B2 * | 7/2006 | Mockli .................... A61Q 5/10 8/405 |
| 2002/0138919 A1 | 10/2002 | Lim et al. |
| 2004/0205909 A1 | 10/2004 | Lim et al. |
| 2017/0196791 A1 | 7/2017 | Nojir |
| 2017/0258695 A1 * | 9/2017 | Consoli .................... A61K 8/55 |
| 2018/0078478 A1 * | 3/2018 | Murphy .............. C09B 29/3665 |
| 2018/0079907 A1 * | 3/2018 | Murphy .............. C07D 487/04 |
| 2018/0105697 A1 * | 4/2018 | Murphy .............. C09B 29/3665 |
| 2020/0197269 A1 | 6/2020 | Gasselin et al. |
| 2020/0289389 A1 | 9/2020 | Monda et al. |

FOREIGN PATENT DOCUMENTS

| | | | | |
|---|---|---|---|---|
| CN | 1487821 A | | 4/2004 | |
| CN | 101379145 A | * | 3/2009 | .............. A61Q 5/10 |
| CN | 111212627 A | | 5/2020 | |
| CN | 113613732 A | * | 11/2021 | .............. A61Q 5/10 |
| EP | 1 366 752 A1 | | 12/2003 | |
| EP | 3 427 720 | | 1/2019 | |
| EP | 3 501 486 | | 3/2021 | |
| JP | 2016-108296 A | | 6/2016 | |
| JP | 2019-151615 A | | 9/2019 | |
| TW | 201627412 A | | 8/2018 | |
| WO | WO 9739727 A1 | * | 10/1997 | .............. A61Q 5/10 |
| WO | WO 2015/186817 A1 | | 12/2015 | |

OTHER PUBLICATIONS

Database GNPD [Online] Mintel; Jul. 8, 2020 (Jul. 8, 2020), anonymous: "Color Blending Gel", XP055785379, 4 pages.
International Search Report and Written Opinion mailed on Jan. 10, 2022 in PCT/EP2021/075790 filed on Sep. 20, 2021 (9 pages).
Extended European Search Report dated Apr. 1, 2021 in European Application 20199263.3 filed on Sep. 30, 2020 (4 pages).

* cited by examiner

*Primary Examiner* — Eisa B Elhilo
(74) *Attorney, Agent, or Firm* — Oblon, McClelland, Maier & Neustadt, L.L.P.

(57) ABSTRACT

A dyeing composition for keratin fibers, including one or more first direct dyes selected from HC Blue 18, HC Red 18, HC Yellow 16, and salts thereof, one or more second direct dyes selected from Disperse Black 9, Acid Yellow 1, 2-amino-6-chloro-4-nitrophenol and salts thereof, and one or more alkalizing agents.

17 Claims, No Drawings

HAIR DYEING COMPOSITION WITH IMPROVED DURABILITY

CROSS REFERENCE TO RELATED APPLICATIONS

This application is a National Stage entry under 35 U.S.C. § 371 of PCT/EP2021/075790, filed on Sep. 20, 2021, and claims priority to European Patent Application No. 20199263.3, filed on Sep. 30, 2020. The entire contents of both are incorporated herein by reference.

FIELD OF THE INVENTION

The present invention is directed to the provision of a dyeing composition for keratin fibers, a method for dyeing and use of certain direct dyes.

BACKGROUND OF THE INVENTION

Direct dyes have been of particular interest of cosmetic industry over the past decade. In contrast to their oxidative counterparts, direct dyes are easier to apply to keratin fibers, but often lack durability on keratin fibers.

Applicant has developed new direct dyes (EP1366752), which complement the availability and color range of the existing ones. A series of the aforementioned developed dyes comprises HC Blue 18, HC Red 18, and HC Yellow 16.

One of the technical challenges with direct dyes in general is their low durability on keratin fibers, which have experienced prior damage due to chemical services such as perming or bleaching. Chemical services alter the internal hair structure and usually allow for improved dye uptake in comparison to virgin hair, but simultaneously direct dyes are also easily washed out. Thus, consumers with prior chemical hair treatments may experience a low durability of the direct dyes, especially after several washes. Moreover, while the color intensity fades over several washes, the hair may experience an additional undesired color shift depending on the different bleeding rates of the individual direct dyes.

In everyday business operation of a hair dresser salon it is also not always easy for the professional to analyze prior hair damage of the customer, as some prior treatments may have already washed out and their effect is not visible anymore. While assuming healthy hair and then performing direct dyeing, it may come to a surprise to the hair dresser as well as the customer that durability of the dyeing treatment is exceptionally low and an undesired color shift is visible after a couple of hair washes. Such experiences will certainly frustrate every party.

In summary, the prior art has not satisfactorily solved the above challenges, and, therefore, there is a real need to develop direct dyeing compositions for keratin fibers, which are effective and have good durability, regardless of the history of chemical treatments.

SUMMARY OF THE INVENTION

Thus, the first object of the present invention is a dyeing composition for keratin fibers, preferably for human keratin fibers, more preferably for human hair, comprising:
a) one or more first direct dye(s) selected from HC Blue 18, HC Red 18, and/or HC Yellow 16, and/or their salt(s), and/or mixtures,
b) one or more second direct dye(s) selected from Disperse Black 9, Acid Yellow 1, 2-amino-6-chloro-4-nitrophenol and/or their salt(s), and/or their mixtures,
c) one or more alkalizing agent(s).

The second object of the present invention is a two-part hair dyeing composition comprising a first composition as defined above and a second aqueous composition having a pH in the range of 1 to 6 and optionally comprising one or more oxidizing agent(s), preferably hydrogen peroxide.

The third object of the present invention is a method for dyeing keratin fibers, preferably human keratin fibers, more preferably human hair, comprising the steps of:
i) providing the composition as defined above and optionally mixing it with a second aqueous composition having a pH in the range of 1 to 6 and optionally comprising an oxidizing agent, preferably hydrogen peroxide, to yield a ready-to-use composition having a pH in the range of 7 to 12,
ii) applying the ready-to-use composition onto keratin fibers and leaving it for a time period in the range of 1 min to 60 min,
iii) optionally rinsing-off the keratin fibers and optionally drying the keratin fibers.

The fourth object of the present invention is a method for dyeing keratin fibers, preferably human keratin fibers, more preferably human hair, comprising the steps of:
x) applying an aqueous composition onto keratin fibers having a pH in the range of 7 to 12 and comprising one or more compound(s) according to group a) and group c) as defined above,
xi) leaving the composition of step x) onto keratin fibers for a time period in the range of 1 min to 60 min, and optionally rinsing-off the keratin fibers and optionally drying the keratin fibers,
xii) applying an aqueous composition onto keratin fibers having a pH in the range of 3 to 12 and comprising one or more compound(s) according to group b) and group c) as defined above,
xiii) leaving the composition of step xii) onto keratin fibers for a time period in the range of 1 min to 60 min, optionally rinsing-off the keratin fibers and optionally drying the keratin fibers.

The fifth object of the present invention is a use of a composition comprising compounds of groups b) and c) as defined above for improving wash fastness of a composition comprising compounds groups a) and c) as defined above on keratin fibers, preferably human keratin fibers, more preferably human hair, further more preferably on human hair which has undergone prior chemical services.

The sixth object of the present invention is a kit-of-parts for dyeing of keratin fibers, preferably human keratin fibers, more preferably human hair comprising the following compositions:
a composition comprising the compounds of groups a) and c) as defined above,
a composition comprising the compounds of groups b) and c) as defined above,
optionally an aqueous oxidizing composition having a pH in the range of 1 to 6 and preferably comprising hydrogen peroxide.

DETAILED DESCRIPTION OF THE INVENTION

Inventors of the present invention have unexpectedly found out that the combination of one or more hair dyes selected from HC Blue 18, HC Red 18, HC Yellow 16, and/or their salt(s), and/or their mixtures with other direct dyes selected from Disperse Black 9, Acid Yellow 1, 2-amino-6-chloro-4-nitrophenol, and/or their salt(s), and/or their mixtures improves the dyeing result and wash fastness of HC Blue 18, HC Red 18, HC Yellow 16, and/or their salt(s), and/or their mixtures on keratin fibers, in particular of keratin fibers with prior damage by chemical services. The combination of the aforementioned dyes allows for dyeing of the customer's hair without the necessity of prior analysis of hair health. Thus, any unexpected low durability and off-tone fading over several washes can be prevented and the resulting hair color is homogenous, intense, and brilliant.

Dyeing Composition

The present invention is directed to a dyeing composition for keratin fibers, preferably for human keratin fibers, more preferably for human hair, comprising:
a) one or more first direct dye(s) selected from HC Blue 18, HC Red 18, and/or HC Yellow 16, and/or their salt(s), and/or their mixtures,
b) one or more second direct dye(s) selected from Disperse Black 9, Acid Yellow 1, 2-amino-6-chloro-4-nitrophenol and/or their salt(s), and/or their mixtures,
c) one or more alkalizing agent(s).

Compound(s) According to a)

The composition of the present invention comprises one or more first direct dye(s) selected from HC Blue 18, HC Red 18, and/or HC Yellow 16, and/or their salt(s), and/or mixtures as compound(s) according to group a).

It is preferred from the viewpoint of dyeing intensity that the total concentration of one or more first direct dye(s) according to group a) is 0.001% by weight or more, more preferably 0.005% by weight or more, further more preferably 0.01% by weight or more, calculated to the total weight of the composition.

It is preferred from the viewpoint of cosmetic safety and cost of goods that the total concentration of one or more first direct dye(s) according to group a) is 1% by weight or less, more preferably 0.75% by weight or less, further more preferably 0.5% by weight or less, calculated to the total weight of the composition.

For attaining the above-mentioned effects, it is preferred that the total weight of one or more first direct dye(s) according to group a) is in the range of 0.001% to 1% by weight, preferably in the range of 0.005% to 0.75% by weight, further more preferably in the range of 0.01% to 0.5% by weight, calculated to the total weight of the composition.

Compound(s) According to b)

The composition of the present invention comprises one or more second direct dye(s) selected from Disperse Black 9, Acid Yellow 1, 2-amino-6-chloro-4-nitrophenol and/or their salt(s), and/or their mixtures as compound(s) according to group b).

It is preferred from the viewpoint of wash fastness on bleached keratin fibers that the one or more compound(s) according to group b) is selected from Disperse Black 9 and/or its salt(s), and/or its mixtures.

Thus, the present disclosure also relates to:
A dyeing composition for keratin fibers, preferably for human keratin fibers, more preferably for human hair, comprising:
a) one or more first direct dye(s) selected from HC Blue 18, HC Red 18, and/or HC Yellow 16, and/or their salt(s), and/or their mixtures,
b) one or more second direct dye(s) selected from Disperse Black 9, and/or its salt(s), and/or its mixtures,
c) one or more alkalizing agent(s),
preferably wherein the keratin fibers are bleached keratin fibers.

It is preferred from the viewpoint of wash fastness on permed keratin fibers that the one or more compound(s) according to group b) is selected from Acid Yellow 1 and/or its salt(s), and/or its mixtures.

Thus, the present disclosure also relates to:
A dyeing composition for keratin fibers, preferably for human keratin fibers, more preferably for human hair, comprising:
a) one or more first direct dye(s) selected from HC Blue 18, HC Red 18, and/or HC Yellow 16, and/or their salt(s), and/or their mixtures,
b) one or more second direct dye(s) selected from Acid Yellow 1, and/or its salt(s), and/or its mixtures,
c) one or more alkalizing agent(s),
preferably wherein the keratin fibers are permed keratin fibers.

Another disclosure relates to:
A dyeing composition for keratin fibers, preferably for human keratin fibers, more preferably for human hair, comprising:
a) one or more first direct dye(s) selected from HC Blue 18, HC Red 18, and/or HC Yellow 16, and/or their salt(s), and/or their mixtures,
b) one or more second direct dye(s) being a mixture of Disperse Black 9 and Acid Yellow 1, and/or their salt(s),
c) one or more alkalizing agent(s),
preferably wherein the keratin fibers are permed and/or bleached keratin fibers.

It is preferred from the viewpoint of wash fastness on permed or bleached keratin fibers that the one or more compound(s) according to group b) is selected from 2-amino-6-chloro-4-nitrophenol, and/or its salt(s), and/or its mixtures.

Thus, the present disclosure also relates to:
A dyeing composition for keratin fibers, preferably for human keratin fibers, more preferably for human hair, comprising:
a) one or more first direct dye(s) selected from HC Blue 18, HC Red 18, and/or HC Yellow 16, and/or their salt(s), and/or their mixtures,
b) one or more second direct dye(s) selected from 2-amino-6-chloro-4-nitrophenol, and/or its salt(s), and/or its mixtures,
c) one or more alkalizing agent(s),
preferably wherein the keratin fibers are permed and/or bleached keratin fibers keratin fibers.

It is further preferred from the viewpoint of wash fastness that the total concentration of one or more second direct dye(s) according to group b) is 0.001% by weight or more, more preferably 0.01% by weight or more, still more preferably 0.05% by weight or more, further more preferably 0.1% by weight or more, calculated to the total weight of the composition.

It is further preferred from the viewpoint of cosmetic safety and economic reasons that that the total concentration of one or more second direct dye(s) according to group b) is 2% by weight or less, still more preferably 1% by weight or less, calculated to the total weight of the composition.

For attaining the above-mentioned effects, it is further preferred that the total concentration of one or more second direct dye(s) according to group b) is in the range of 0.001% to 2% by weight, preferably in the range of 0.01% to 1% by weight, more preferably in the range of 0.05% to 1% by weight, calculated to the total weight of the composition.

It is further preferred from the viewpoint of color balancing and wash fastness that the weight ratio of dyes according to group a) to dyes according to group b) is 5 or less, more preferably 3 or less, further more preferably 1.5 or less.

It is further preferred from the viewpoint of wash fastness that the weight ratio of dyes according to group a) to dyes according to group b) is 0.05 or more, more preferably or more, further more preferably 0.15 or more.

For attaining the above-mentioned effects, it is preferred that the weight ratio of dyes according to group a) to dyes according to group b) is in the range of 5 to 0.05, preferably in the range of 3 to 0.1, more preferably in the range of 1.5 to 0.15.

Compound(s) According to c)

The composition of the present invention also comprises one or more alkalizing agent(s) as compound(s) according to group c).

In principle, all alkalizing agents are suitable for the purpose of the present invention, as long as they provide sufficient alkalinity to the composition, i.e. being able to raise the pH of the composition once in contact with water into a range of 7 to 12.

It is preferred from the viewpoint of providing alkalinity and cosmetic safety that one or more compound(s) according to group c) is/are selected from ammonia and/or its salt(s) and/or organic alkalizing agent(s) and/or its/their salt(s).

Particularly preferred organic alkalizing agent(s) as compound(s) according to group c) are selected from organic alkyl and/or alkanol amines and/or their salt(s) according to the following general structure:

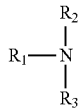

wherein R1, R2, and R3 are independently selected from H, linear C1-C6 alkyl which may be substituted with one hydroxyl group, or branched C3-C12 alkyl or alkanol, wherein at least one of R1, R2, or R3 is different from H, and/or their salts, and/or their mixtures.

Preferably, one or more organic alkalizing agent(s) are selected from alkyl and/or alkanolamine(s) and/or its/their salt(s), more preferably they/it is selected from monoethanolamine, diethanolamine, monoethanol methylamine, monoethanol dimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine, trimethylamine, triethylamine, 2-amino-2-methylpropanol, tris-(hydroxymethyl)-aminomethane and/or its/their salt(s), and/or their mixtures, from the viewpoint of providing alkalinity and cosmetic safety as well as their low odor.

The most preferred alkalizing agent(s) it is selected from monoethanolamine, 2-amino-2-methylpropanol, tris-(hydroxymethyl)-aminomethane and/or its/their salt(s), ammonia and or its salt(s), and/or their mixtures, from the viewpoint of providing alkalinity and cosmetic safety.

It is preferred from the viewpoint of providing alkalinity that the total concentration of compound(s) according to group c), preferably the total concentration of one or more alkanolamine(s) and/or its/their salt(s) and/or ammonia and/or its salt(s), is 0.1% by weight or more, more preferably 0.25% by weight or more, further more preferably by weight or more, calculated to the total weight of the composition.

It is preferred from the viewpoint of providing alkalinity, hair damage, and odor that the total concentration of compound(s) according to group c), preferably the total concentration of one or more alkanolamine(s) and/or its/their salt(s) and/or ammonia and/or its salt(s), is 40% by weight or less, more preferably 30% by weight or less, further more preferably 25% by weight or less, calculated to the total weight of the composition.

For attaining the above-mentioned effects, it is preferred that the total concentration of compound(s) according to group c), preferably the total concentration of one or more alkanolamine(s) and/or its/their salt(s) and/or ammonia and/or its salt(s), is in the range of 0.1% to 40% by weight, preferably in the range of 0.25% to 30% by weight, more preferably in the range of 0.4% to 25% by weight, calculated to the total weight of the composition.

Cosmetic Forms of Composition

The dyeing composition of the present invention is available in various cosmetic forms.

Aqueous Composition

In one aspect of the present invention, the dyeing composition is an aqueous composition.

The term 'aqueous' denotes a composition that comprises a majority of water, i.e., the composition preferably comprises water at 50% by weight or more, further more preferably at 60% by weight or more, still more preferably at 70% by weight or more, still further more preferably at 80% by weight or more, calculated to the total weight of the composition, from the viewpoint of achieving a cosmetically acceptable composition.

It is further preferred from the viewpoint of dyeing intensity that the composition comprises water at 98% by weight or less, more preferably at 95% by weight or less, further more preferably at 92% by weight or less, calculated to the total weight of the composition.

For achieving the above-mentioned effects, it is preferred that the total concentration of water is in the range of 50% to 98% by weight, more preferably in the range of 60% to 95% by weight, further more preferably in the range of 70% to 92% by weight, still more preferably in the range of 80% to 92% by weight, calculated to the total weight of the composition.

It is preferred from the viewpoint of dyeing performance that the pH of the aqueous composition is 7 or more, more preferably the pH is 7.5 or more, further more preferably the pH is 8 or more, still further more preferably the pH is 8.5 or more.

It is preferred from the viewpoint of hair damage and dyeing performance that the pH of the composition is 12 or less, more preferably the pH is 11 or less, still more preferably the pH is 10.8 or less.

For attaining the above mentioned effects, it is preferred that the aqueous dyeing composition has a pH in the range of 7 to 12, preferably in the range of 7.5 to 11, more preferably in the range of 8 to 10.8, further more preferably in the range of 8.5 to 10.8.

From the viewpoint of selection of compound(s) according to group c), any of the listed compounds from above are suitable for adjusting the pH of the aqueous composition.

Thus, the present disclosure is also directed to an aqueous dyeing composition for keratin fibers, preferably for human keratin fibers, more preferably for human hair, having a pH in the range of 7 to 12, preferably in the range of 7.5 to 11, more preferably in the range of 8 to 10.8, further more preferably in the range of 9 to 10.8 comprising:
- a) one or more first direct dye(s) selected from HC Blue 18, HC Red 18, and/or HC Yellow 16, and/or their salt(s), and/or mixtures,
- b) one or more second direct dye(s) selected from Disperse Black 9, Acid Yellow 1, 2-amino-6-chloro-4-nitrophenol and/or their salt(s), and/or their mixtures,
- c) one or more alkalizing agent(s).
- wherein the composition comprises water at 50% by weight or more, calculated to the total weight of the composition.

Liquid Composition Comprising Less than 1% by Weight of Water

In another aspect of the present invention, the dyeing composition is a liquid composition at 25° C. and atmospheric pressure comprising one or more organic solvent(s) as compound(s) according to group d) and less than 1% by weight of water, calculated to the total weight of the composition. Preferably, the composition is anhydrous, from the viewpoint of dye stability.

The term 'liquid' denotes a physical state at 25° C. and atmospheric pressure, i.e., the dyeing composition is liquid at room temperature.

The term 'anhydrous' denotes a composition, which is free of added water. This does not exclude the presence of residual moisture from air or crystal water bound to ingredients.

For this aspect of the present invention, the composition may comprise one or more organic solvent(s) as compound (s) according to group d).

The organic solvent(s) may be selected to dissolve the compounds according to groups a) to c). Preferred solvents are mono-, di-, and trivalent alcohols and/or their mixtures.

Preferred mono-, di-, and trivalent alcohols from the viewpoint of cosmetic safety and dissolution capacity are ethanol, n-propanol, isopropanol, propylene glycol, ethylene glycol, benzyl alcohol, phenoxyethanol, and glycerol, and/or their mixtures.

It is further preferred from the viewpoint of solution stability that the total concentration of compound(s) according to group d) is 75% by weight or more, more preferably 80% by weight or more, further more preferably 85% by weight or more, calculated to the total weight of the composition.

It is further preferred from the viewpoint of dyeing intensity that the total concentration of compound(s) according to group d) is 98% by weight or less, more preferably 95% by weight or less, further more preferably 92% by weight or less, calculated to the total weight of the composition.

For attaining the above-mentioned effects, it is preferred that the total concentration of compound(s) according to group d) is in the range of 75% to 98% by weight, more preferably 80% to 95% by weight, further more preferably in the range of 85% to 92% by weight, calculated to the total weight of the composition.

Thus, the present disclosure is also directed to an anhydrous dyeing composition for keratin fibers, preferably for human keratin fibers, more preferably for human hair, comprising:
- a) one or more first direct dye(s) selected from HC Blue 18, HC Red 18, and/or HC Yellow 16, and/or their salt(s), and/or mixtures,
- b) one or more second direct dye(s) selected from Disperse Black 9, Acid Yellow 1, 2-amino-6-chloro-4-nitrophenol and/or their salt(s), and/or their mixtures,
- c) one or more alkalizing agent(s),
- wherein the total concentration of compound(s) according to group d) is 75% by weight or more, calculated to the total weight of the composition.

Powder Composition

In one aspect of the present invention, the dyeing composition may be a powder composition.

The term 'powder' denotes a solid composition at 25° C. and atmospheric pressure. The term relates to freely flowing powders as well as compressed powders such as tablets. The powder composition may also comprise water as long as its nature of the solid state at 25° C. is unchanged. Depending on the type of powder, a water content of 10% by weight or more, calculated to the total weight of the composition, may be acceptable.

It is preferred from the viewpoint of composition stability and convenience of use that the dyeing composition comprises one or more pulverulent excipient as compound(s) according to group e).

The term 'excipient' denotes a compound, which may act as filling material and dispersant for the other compounds of the dyeing composition and do not react with the dyes and the alkalizing agent, and, thus, confer the powder a high degree of storage stability over an extended period of time.

The dyeing composition of the present invention may comprise an organic and/or an inorganic pulverulent excipient in which the alkalizing agent and direct dyes are dispersed.

Suitable organic and/or an inorganic pulverulent excipients are, for example, diatomaceous earth, kaolin, bentonite, starch especially corn, tapioca, rice, wheat and potato, nylon powder, montmorillonit, gypsum, sawdust and perlite.

The total concentration of organic and/or an inorganic pulverulent excipient preferably is 50% by weight or more, more preferably 55% by weight or more, further more preferably 60% by weight or more, still further more preferably 65% by weight or more, even further more preferably 70% by weight or more, even more preferably 75% by weight or more, calculated to the total of the composition, from the viewpoint of achieving good dispersability of the direct dyes in the powder and quick dissolution of the powder.

The total concentration of organic and/or an inorganic pulverulent excipient preferably is 98% by weight or less, more preferably 95% by weight or less, further more preferably 90% by weight or less, calculated to the total of the composition, from the viewpoint of achieving good dispersability of the direct dyes in the powder and formulation freedom.

For attaining the above mentioned effects, the total concentration of organic and/or an inorganic pulverulent excipient preferably is in the range of 50% to 98% by weight, more preferably in the range of 55% to 95% by weight, further more preferably in the range of 60% to 90% by weight, still further more preferably 65% to 90% by weight, still further more preferably 70% to 90% by weight, even more preferably 75% to 90% by weight, calculated to the total weight of the composition.

Thus, the present disclosure is also directed to a dyeing composition for keratin fibers, preferably for human keratin fibers, more preferably for human hair, comprising:
- a) one or more first direct dye(s) selected from HC Blue 18, HC Red 18, and/or HC Yellow 16, and/or their salt(s), and/or mixtures,
- b) one or more second direct dye(s) selected from Disperse Black 9, Acid Yellow 1, 2-amino-6-chloro-4-nitrophenol and/or their salt(s), and/or their mixtures,
- c) one or more alkalizing agent(s),
- e) one or more pulverulent excipient(s), wherein the composition is a powder composition, and preferably wherein the total concentration of compound(s) according to group e) is 50% by weight or more, calculated to the total weight of the composition.

Lipophilic Compound(s) According to Group f)

It is preferred that the dyeing composition of the present invention comprises one or more lipophilic compound(s) as compound(s) according to group f).

The term 'lipophilic' denotes a liquid compound at 25° C. and atmospheric pressure and does not fully mix with water under the aforementioned conditions.

Preferably, lipophilic compounds are selected from fatty alcohols, fatty acids, waxes, vegetable oils, petrolatum based products, silicones, aminated silicones, and compounds according to the general structure:

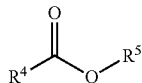

wherein R4 is selected from linear or branched, saturated or unsaturated alkyl with C11 to C21 and optionally modified with 1 hydroxyl group, and R5 is selected from linear or branched, saturated or unsaturated alkyl with C3 to C18, preferably the compound is ethylhexyl hydroxystearate, in the viewpoint of film homogeneity and pigment deposition Suitable fatty alcohols are linear or branched, saturated or unsaturated fatty alcohols with C12 to C22 are lauryl alcohol, tridecyl alcohol, myristyl alcohol, pentadecyl alcohol, cetyl alcohol, palmitoleyl alcohol, heptadecyl alcohol, stearyl alcohol, nonadecyl alcohol, arachidyl alcohol, behenyl alcohol, and/or their mixtures.

Suitable fatty acids are saturated or unsaturated fatty acids with or without a hydroxyl group. Suitable are myristoleic acid, palm itoleic acid, oleic acidlinoleic acid, arachidonic acid, and/or their mixtures.

Suitable compounds according to the general structure from above are isopropyl palmitate, isopropyl myristate, octyl palmitate, isocetyl palmitate, octyl stearate, oleyl oleate, ethylhexyl hydroxystearate, myristyl myristate, behenyl behenate, and/or their mixtures.

Suitable vegetable oils are jojoba oil, avocado oil, sunflower seed oil, walnut oil, peanut oil, olive oil, rapeseed oil, cottonseed oil, palm oil, sesame oil, soybean oil, coconut oil, safflower oil, almond oil, macadamia nut oil, grapefruit seed oil, lemon kernel oil, orange kernel oil, apricot kernel oil, castor oil, and/or their mixtures.

Suitable petrolatum-based products are liquid paraffins, especially paraffinum perliquidum and paraffinum subliquidum, and mineral oil, in particular white mineral oil, and/or their mixtures.

Suitable silicones are dimethylpolysiloxanes, and modified silicones (for example, amino-modified silicones, fluorine-modified silicones, alcohol-modified silicones, polyether-modified silicones, epoxy-modified silicones, or alkyl-modified silicones), but dimethylpolysiloxane, polyether-modified silicones and amino-modified silicones are preferred. Amino-modified silicones are commonly known under their CTFA name amodimethicone.

Specific examples of suitable commercially available amodimethicone oils such as SF8452C, SS-3551 (all by Dow Corning Toray Co., Ltd.), KF-8004, KF-8675, and KF-8015 (all by Shin-Etsu Chemical Co., Ltd.), and amodimethicone emulsions such as SM8704C, SM8904, BY22-079, FZ-4671, and FZ-4672 (all by Dow corning Toray Co., Ltd.).

The amino-modified silicone may be any silicone having an amino group or a quaternary ammonium group, and examples thereof include amine-modified silicone oil having all or a part of the terminal hydroxyl groups capped with a methyl group for example, and an amodimethicone which does not have the terminals capped.

The composition may comprise one or more waxes. Suitable non-limiting and preferred examples are petrolatum, ozokerit, carnauba wax, paraffin, lanolin wax, candelila wax, bees wax, microcrystalline wax and cocoglycerides.

The dyeing composition may comprise lipophilic compound(s) according to group f) form the viewpoint of dyeing intensity, preferably at a total concentration of 0.1% by weight or more, more preferably at 0.5% by weight or more, further more preferably at 1% by weight or more, calculated to the total weight of the composition.

The dyeing composition may comprise lipophilic compound(s) according to group f) form the viewpoint of dyeing intensity and rinsibility of keratin fibes, preferably at a total concentration of 40% by weight or less, more preferably at 30% by weight or less, further more preferably at 25% by weight or less, calculated to the total weight of the composition.

For attaining the above mentioned effects, it is preferred that the dyeing composition comprises lipophilic compound(s) according to f) at a total concentration in the range of 0.1% to 40% by weight, more preferably in the range of 0.5% to 30% by weight, further more preferably in the range of 1% to 25% by weight, calculated to the total weight of the composition.

In one aspect of the present invention, the disclosure is also directed to an aqueous dyeing composition for keratin fibers, preferably for human keratin fibers, more preferably for human hair, having a pH in the range of 7 to 12, preferably in the range of 7.5 to 11, more preferably in the range of 8 to 10.8, further more preferably in the range of 9 to 10.8 comprising:
- a) one or more first direct dye(s) selected from HC Blue 18, HC Red 18, and/or HC Yellow 16, and/or their salt(s), and/or mixtures,
- b) one or more second direct dye(s) selected from Disperse Black 9, Acid Yellow 1, 2-amino-6-chloro-4-nitrophenol and/or their salt(s), and/or their mixtures,
- c) one or more alkalizing agent(s), wherein the composition comprises water at 50% by weight or more, calculated to the total weight of the composition, and wherein the composition is an emulsion and comprises one or more compound(s) according to group f) selected from fatty alcohols having an branched or linear, saturated or unsaturated carbon chain length in the range of C12 to C22, fatty acids having an branched or linear, saturated or unsaturated carbon chain length in the range of C12 to C22, ester oils, vegetable oils, silicone oil, paraffin oils.

In another aspect of the present invention, the disclosure also relates to a dyeing composition for keratin fibers, preferably for human keratin fibers, more preferably for human hair, comprising:
- a) one or more first direct dye(s) selected from HC Blue 18, HC Red 18, and/or HC Yellow 16, and/or their salt(s), and/or mixtures,
- b) one or more second direct dye(s) selected from Disperse Black 9, Acid Yellow 1, 2-amino-6-chloro-4-nitrophenol and/or their salt(s), and/or their mixtures,
- c) one or more alkalizing agent(s),
- e) one or more pulverulent excipient(s),
- wherein the composition is a powder composition, and preferably wherein the total concentration of compound(s) according to e) is 50% by weight or more, calculated to the total weight of the composition, and
- wherein the composition comprises one or more lipophilic compound(s) according to group f), preferably at a total concentration of 1% by weight or more.

The artisan will note that the latter composition is either a dust-free dyeing powder or a dyeing paste.

Surfactants as Compound(s) According to g)

It is further preferred from the viewpoint of mixability of the dyeing composition and wetting of keratin fibers that the composition of the present invention further comprises one or more surfactant(s) as compound(s) according to group g), more preferably selected from non-ionic, cationic, anionic, zwitterionic/amphoteric surfactant(s).

Anionic surfactants suitable are in principle known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolam ides, and the alkali salts thereof, as well as the salts of long-chain mono- and dialkyl phosphates. Preferred anionic surfactants are alkyl sulphate surfactants especially lauryl sulphate and its salts.

Further suitable surfactants are nonionic surfactants. Non-limiting examples are long-chain fatty acid mono- and dialkanolam ides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic, palmitic, myristic and lauric acid esters, fatty acid polyglycol esters or poly-condensates of ethyleneoxide and propyleneoxide, as they are on the market, for example, under the trade name "Pluronics®", as well as fatty alcohol ethoxylates, $C_{10}$-$C_{22}$-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 100, preferably about 10 and about 30.

Suitable amphoteric/zwitterionic surfactants are in particular the various known betaines such as alkyl betaines, fatty acid am idoalkyl betaines and sulfobetaines, for example, lauryl hydroxysulfobetaine; long-chain alkyl amino acids, such as cocoaminoacetate, cocoaminopropionate and sodium cocoamphopropionate and—acetate are also suitable.

Typical cationic surfactants are cetyl trimethyl ammonium chloride, stearyl trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

It is preferred from the viewpoint of composition stability, wetting of keratin fibers, and ingredient dispersability that the total concentration of compound(s) according to group g) is 0.1% by weight or more, preferably 0.2% by weight or more, further more preferably 0.25% by weight or more, calculated to the total weight of the composition.

It is preferred from the viewpoint of composition stability, wetting of keratin fibers, and ingredient dispersability that the total concentration of compound(s) according to group g) is 5% by weight or less, preferably 4% by weight or less, further more preferably 2.5% by weight or less, calculated to the total weight of the composition.

For attaining the above-mentioned effects, it is preferred that the total concentration of compound(s) according to group g) is in the range of 0.1% to 5% by weight, more preferably 0.2% to 4% by weight, further more preferably 0.2% to 2.5% by weight, calculated to the total weight of the composition.

Dyes Different From Groups a) and b)

The dyeing composition of the present invention may comprise one or more dye compound(s) different from the ones of groups a) and b), preferably selected from oxidative dye precursor(s), oxidative dye coupler(s), and/or direct dye(s).

Suitable oxidative dye precursors classes are p-phenylendiamines, p-aminophenols, and heterocyclic compounds such as diaminopyrazols and substituted pyrimidines, and suitable coupling substances are resorcinols, m-aminophenols, m-phenylendiamines, pyridines and substituted derivatives, and naphthols.

Suitable oxidative dye couplers are 5-amino-2-methylphenol, 2-methyl-5-hydroxyethylaminophenol, 2,4,-diaminophenoxyethanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hy-droxyethylamino)benzene, 1-amino-3-[bis(2'-hydroxy-ethyl) amino] benzene, α-naphthol, 4,6-dichlororesorcinol, 1,3-diaminotoluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2- methoxyphenol and/or 1-methoxy-2-amino-4-(2'-hydroxyethyl amino)-benzene, and/or their salts, and/or their mixtures.

The dyeing composition of the present invention may comprise the oxidative dye couplers and/or precursors at approximately the equimolar proportions, for example at a total concentration in the range of 0.001% to 5%, calculated to the total weight of the composition.

Direct dyes other than compounds according to the ones of group a) and b) may be selected from cationic, anionic and/or non-ionic direct dyes.

The total concentration of one or more direct dyes other than the ones of groups a) and b) in the composition of the present invention, if present, preferably is 0.01% by weight or more, more preferably 0.05% by weight or more, further more preferably 0.1% by weight or more, calculated to the total weight of the composition, from the viewpoint of sufficiently dyeing the keratin fibers.

The total concentration of one or more direct dyes other than the ones of groups a) and b) in the composition of the present invention, if present, preferably is 10% by weight or less, more preferably 9% by weight or less, further more preferably 7.5% by weight or less, further more preferably 6% by weight or less, even more preferably 4% by weight or less, calculated to the total weight of the composition, from the viewpoint of economic reasons and formulation freedom.

For attaining the above mentioned effects, the total concentration of one or more direct dyes other than the ones of groups a) and b) in the composition of the present invention, if present, is in the range of 0.01% to 10% by weight, preferably 0.05% to 9% by weight, more preferably 0.1% to 7.5% by weight, further more preferably 0.1% to 6% by weight, even more preferably 0.1% to 4% by weight, calculated to the total weight of the composition.

In one aspect of the present invention, the composition of the present invention may also comprise one or more oxidative dye coupler(s) and/or precursors.

Two-Part Composition

The present invention is also directed to a two-part hair dyeing composition comprising a first composition as defined above and a second aqueous composition having a pH in the range of 1 to 6 and optionally comprising one or more oxidizing agent(s), preferably hydrogen peroxide.

The second aqueous composition preferably comprises hydrogen peroxide as an oxidizing agent. Suitable concentrations range from 0.1% to 20% by weight, preferably 0.25% to 15% by weight, and more preferably 0.5% to 12% by weight, calculated to the total weight of the second aqueous composition.

The pH of the second aqueous composition preferably is in the range of 1.5 to 5, more preferably in the range of 2 to 4.5, adjusted by suitable acids and bases.

It is further preferred from the viewpoint of mixability with the first composition that the second aqueous composition comprises one or more lipophilic compound(s) according to f), as laid out above for the dyeing composition. In such a case, the second aqueous composition is an emulsion and preferably also comprises one or more surfactant(s) as compound(s) according to g), as laid out above for the dyeing composition.

First and second compositions in this aspect of the present invention are intended to be mixed directly prior to application onto keratin fibers.

Method for Dyeing

The present invention is also directed to a method for dyeing keratin fibers, preferably human keratin fibers, more preferably human hair, comprising the steps of:
  i) providing the composition as defined above and optionally mixing it with a second aqueous composition as defined above to yield a ready-to-use composition having a pH in the range of 7 to 12,
  ii) applying the ready-to-use composition onto keratin fibers and leaving it for a time period in the range of 1 min to 60 min,
  iii) optionally rinsing-off the keratin fibers and optionally drying the keratin fibers.

It is preferred from the viewpoint of color intensity that the pH of the ready-to-use composition as defined in step i) is in the range of 8 to 11, more preferably in the range of 8.5 to 10.5.

It is further preferred from the viewpoint of dyeing intensity and dyeing method economy that the leave-on time as defined in step ii) is in the range of 2 min to 45 min, more preferably in the range of 5 min to 40 min, further more preferably in the range of 10 min to 30 min.

It is further preferred from the viewpoint of cosmetic safety that the keratin fibers are rinsed-off in step iii).

The method is particularly suitable to be applied onto chemically damaged keratin fibers, more preferred on bleached and/or permed keratin fibers.

The present invention is also directed to a method for dyeing keratin fibers, preferably human keratin fibers, more preferably human hair, comprising the steps of:
  x) applying an aqueous composition onto keratin fibers having a pH in the range of 7 to 12 and comprising one or more compound(s) according to group a) and group c) as defined above,
  xi) leaving the composition of step x) onto keratin fibers for a time period in the range of 1 min to 60 min, and optionally rinsing-off the keratin fibers and optionally drying the keratin fibers,
  xii) applying an aqueous composition onto keratin fibers having a pH in the range of 3 to 12 and comprising one or more compound(s) according to group b) and group c) as defined above,
  xiii) leaving the composition of step xii) onto keratin fibers for a time period in the range of 1 min to 45 min, optionally rinsing-off the keratin fibers and optionally drying the keratin fibers.

It is preferred from the viewpoint of improving wash fastness that step xii) is performed without time delay after step xi), or with a delay of 1 to 5 washes of keratin fibers between performing steps xi) and xii).

The method is particularly suitable to be applied onto chemically damaged keratin fibers, more preferred on bleached and/or permed keratin fibers.

It is preferred from the viewpoint of cosmetic safety that the keratin fibers are rinsed off in step xiii).

It is further preferred from the viewpoint of cosmetic safety and dyeing intensity that the pH of the composition as defined in step xii) is in the range of 4 to 11.5, more preferably in the range of 4.5 to 11, further more preferably in the range of 7 to 10.8.

Use for Improving Wash Fastness

The present invention is also directed to the use of a composition comprising compounds of groups b) and c) as defined above for improving wash fastness of a composition comprising compounds groups a) and c) as defined above on keratin fibers, preferably human keratin fibers, more preferably human hair, further more preferably on human hair which has undergone prior chemical services.

It is further preferred that the use is onto bleached and/or permed keratin fibers.

Kit-of-Parts

The present invention is also directed to a kit-of-parts for dyeing of keratin fibers, preferably human keratin fibers, more preferably human hair comprising the following compositions:
- a composition comprising the compounds of groups a) and c) as defined above,
- a composition comprising the compounds of groups b) and c) as defined above,
- optionally an aqueous oxidizing composition having a pH in the range of 1 to 6 and preferably comprising hydrogen peroxide.

It is preferred from the viewpoint of dyeing intensity and cosmetic safety that the composition comprising compounds of groups b) and c) is an aqueous composition having a pH in the range of 3 to 12, preferably in the range of 4.5 to 11, more preferably in the range of 7 to 10.8. The term 'aqueous' denotes a composition, which comprises 50% by weight of water or more, calculated to the total weight of the composition.

It is further preferred for commercial reasons that the composition comprising compounds of groups a) and c) is an aqueous composition having a pH in the range of 7 to 12, preferably in the range of 8 to 11, more preferably in the range of 8.5 to 10.8. The same definition of the term 'aqueous' applies.

The following examples are to illustrate the present invention, but not to limit it.

EXAMPLES

The following dyeing compositions of tables 1 and 2 were prepared by dissolving the alkalizing agent first, and then subsequently adding the dyes to water. Finally, the pH was adjusted. The dye concentrations were selected and matched to yield a comparable degree of dyeing on white goat hair.

TABLE 1

| | | Ingredients | Comp. ex. 1 | | Comp. ex. 2 | | Inv. ex. 1 | | Inv. ex. 2 | | Inv. ex. 3 | |
|---|---|---|---|---|---|---|---|---|---|---|---|---|
| Composition [% by weight] | c) | 2-aminomethylpropanol | 4.74 | | 4.74 | | 4.74 | | 4.74 | | 4.74 | |
| | a) | HC Blue 18 | 0.019 | | 0.019 | | 0.019 | | 0.019 | | 0.019 | |
| | | HC Red 18 | 0.005 | | 0.005 | | 0.005 | | 0.005 | | 0.005 | |
| | | HC Yellow 16 | 0.025 | | 0.09 | | 0.025 | | 0.025 | | 0.025 | |
| | b) | Disperse black 9 | — | | — | | 0.1 | | — | | 0.1 | |
| | | Acid Yellow 1 | — | | — | | — | | 1.0 | | 1.0 | |
| | | NaOH/HCl | | | | | Ad pH 10.6 | | | | | | |
| | | Water | | | | | Ad 100.0 | | | | | | |
| Evaluation | | | C* | h | C* | h | C* | h | C* | h | C* | h |
| | | Virgin Hair | −0.80 | −34.33 | −10.50 | −7.61 | −1.80 | 1.37 | −1.10 | 5.25 | 8.37 | −2.33 |
| | | Permed hair | 4.15 | −77.29 | −17.06 | −77.40 | −12.04 | −98.67 | −14.30 | 21.23 | −6.68 | 11.63 |
| | | Bleached hair | 3.73 | −49.26 | −8.66 | −116.86 | −5.64 | 0.51 | −27.01 | −117.95 | 11.63 | 12.75 |

TABLE 2

| | | Ingredients | Comp. ex. 3 | | Comp. ex. 4 | | Inv. ex. 4 | | Inv. ex. 5 | |
|---|---|---|---|---|---|---|---|---|---|---|
| Composition [% by weight] | c) | 2-aminomethylpropanol | 4.74 | | 4.74 | | 4.74 | | 4.74 | |
| | a) | HC Blue 18 | 0.019 | | 0.019 | | 0.019 | | 0.019 | |
| | | HC Red 18 | 0.005 | | 0.005 | | 0.005 | | 0.005 | |
| | | HC Yellow 16 | 0.025 | | 0.025 | | 0.025 | | 0.025 | |
| | b) | Disperse black 9 | — | | — | | — | | — | |
| | | Acid Yellow 1 | — | | — | | — | | 0.5 | |
| | | 2-amino-6-chloro-4-nitrophenol | — | | — | | 0.035 | | 0.035 | |
| | | Sodium picramate | 0.035 | | — | | — | | — | |
| | | HC yellow 13 | — | | 0.035 | | — | | — | |
| | | NaOH/HCl | | | | | Ad pH 10.6 | | | |
| | | Water | | | | | Ad 100.0 | | | |
| Evaluation | | | C* | h | C* | h | C* | h | C* | h |
| | | Virgin Hair | −10.77 | 28.34 | −6.56 | −5.57 | −9.97 | 13.72 | 6.56 | 23.58 |
| | | Permed hair | 6.94 | −162.56 | −7.39 | −130.71 | −21.13 | 18.93 | −5.99 | 26.77 |
| | | Bleached hair | −7.18 | 175.37 | −12.81 | −94.98 | 1.95 | 15.82 | −2.56 | 17.76 |

Discussion of Results

Comparative examples 1 and 2 illustrate that wash fastness on bleached or permed hair is poor. $\Delta h^*$ angle shifts by over 200 degrees in comparison to virgin hair indicating a different color shade on bleached or permed hair.

Comparative examples 3 and 4 illustrate that other hair direct dyes such as sodium picramate (yellow) and HC yellow 13 (yellow) did not remedy the stark shift of the hue angle on bleached or permed hair.

Inventive example 1 illustrates that Disperse black 9 improves wash fastness on bleached hair, and Acid Yellow 1 improves wash fastness on permed hair, as illustrated in inventive example 2. By combination of both dyes, wash fastness is improved on bleached and permed hair simultaneously. Likewise, inventive example 4 illustrates that 2-amino-6-chloro-4-nitrophenol improves wash fastness on bleached and permed hair and can also be used in combination with the other direct dyes (exemplified in inventive example 5).

Methods

Hair Preparation

Commercially available goat hair (15 cm long, 2 g per bundle) was pre-washed and blow-dried prior to any treatment.

For hair having undergone perm treatment, a commercial perm was performed, which is available under the trade name Structure and Shine under the brand name Goldwell. The first step was the application of a reducing composition comprising thioglycolic acid, leaving it for 20 min on the hair, then rinsing it off and applying an oxidizing composition comprising hydrogen peroxide. The oxidizing composition was left for 15 min onto the hair and then the hair was shampooed and blow-dried. The hair obtained by this method was used for the dyeing experiments on permed hair.

For the hair undergone bleach treatment, a commercial bleach was performed, which is available under the trade name Oxycur Platin from Goldwell. The bleaching powder comprised persalts and was mixed with an oxidizing composition comprising hydrogen peroxide in a weight ration 1:1 prior to application onto the hair. Then to hair was applied the ready-to-use mixture and it was left for 20 min. The hair was then rinsed-off, shampooed, and blow-dried. The hair obtained by this method was used for the dyeing experiments on bleached hair.

Hair Dyeing 2 g of each of the compositions presented above were applied to the hair as prepared above and left for 20 min at ambient temperature. The hair was then rinsed-off with water and blow-dried.

Colormetric measurements were conducted on the hair streaks with a color-difference meter using the CIE colorimetric system (L*, a*, b*). The values are termed 'freshly dyed' for further calculation purposes.

Wash Fastness Experiments

Each hair streak was then placed in a shaking bath comprising a 1.5% by weight solution of sodium laureth sufate at 40° C. and 100 rpm for 30 min. Then the hair streaks were rinsed-off with water and blow dried. Colormetric measurements were conducted again and the (L*, a*, b*) values were obtained. They are termed 'washed' for further calculation purposes.

C* and h Calculations

For assessing the color differences between washed and freshly colored hair, each a* and b* values of the washed samples were subtracted from the freshly colored ones.

C* was then calculated by the following equation:

$$C^* = \sqrt{a^{*2} + b^{*2}}$$

h was then calculated by the following equation $$h = \tan^{-1}\left(\frac{b^*}{a^*}\right)$$

C* or h values in tables 1 and 2 for permed or bleached hair report the differences between washed—freshly colored hair (wash fastness). The closer the values to 0, the lower the color fading of the dyes.

The following examples are within the scope of the present invention.

Inventive Example 6

The following dyeing composition can be produced by conventional formulation techniques.

|  | % by weight |
| --- | --- |
| Aminomethyl propanol | 5.0 |
| HC Blue 18 | 0.25 |
| HC Red 18 | 0.25 |
| HC Yellow 16 | 0.25 |
| Disperse Black 9 | 0.2 |
| Acid yellow 1 | 0.2 |
| 1,2-propylene glycol | ad 100.0 |

Inventive Example 7

The following dyeing composition can be produced by conventional formulation techniques.

|  | % by weight |
| --- | --- |
| Aminomethyl propanol | 5.0 |
| HC Blue 18 | 0.25 |
| HC Red 18 | 0.25 |
| HC Yellow 16 | 0.25 |
| Disperse Black 9 | 0.2 |
| Acid yellow 1 | 0.2 |
| Diatomaceous Earth | to 100 |

The following dyeing compositions can be produced by conventional formulation techniques.

| Ingredients | Inv. Ex. 8 | Inv. Ex. 9 | Inv. Ex. 10 | Inv. Ex. 11 | Inv. Ex. 12 | Inv. Ex. 13 | Inv. Ex. 14 | Inv. Ex. 15 | Inv. Ex. 16 |
|---|---|---|---|---|---|---|---|---|---|
| HC Red 18 | 0.005 | 0.005 | 0.005 | 0.005 | 0.005 | 0.005 | 0.005 | 0.005 | 0.005 |
| HC Blue 18 | 0.02 | 0.02 | 0.02 | 0.02 | 0.02 | 0.02 | 0.02 | 0.02 | 0.02 |
| HC Yellow 16 | 0.025 | 0.025 | 0.025 | 0.025 | 0.025 | 0.025 | 0.025 | 0.025 | 0.025 |
| Disperse Black 9 | 0.1 | 0.1 | 0.1 | 0.1 | 0.1 | 0.1 | 0.1 | 0.1 | 0.1 |
| Acid Yellow 1 | 0.5 | 0.5 | 0.5 | 0.5 | 0.5 | 0.5 | 0.5 | 0.5 | 0.5 |
| Disperse Violet 1 | 0.05 | — | — | — | — | — | — | — | — |
| HC Blue 11 | — | 0.05 | — | — | — | — | — | — | — |
| HC Yellow 4 | — | — | 0.05 | — | — | — | — | — | — |
| HC Violet 2 | — | — | — | 0.05 | — | — | — | — | — |
| HC Violet BS | — | — | — | — | 0.05 | — | — | — | — |
| Basic Yellow 82 | — | — | — | — | — | 0.05 | — | — | — |
| HC Blue 12 | — | — | — | — | — | — | 0.05 | — | — |
| Basic Violet 2 | — | — | — | — | — | — | — | 0.05 | — |
| Basic Blue 77 | — | — | — | — | — | — | — | — | 0.05 |
| 2-aminomethyl propanol | 1.0 | 1.0 | 1.0 | 1.0 | 1.0 | 1.0 | 1.0 | 1.0 | 1.0 |
| Ammonia | 0.5 | 0.5 | 0.5 | 0.5 | 0.5 | 0.5 | 0.5 | 0.5 | 0.5 |
| Ethanol | 3.0 | 3.0 | 3.0 | 3.0 | 3.0 | 3.0 | 3.0 | 3.0 | 3.0 |
| Propylene glycol | 5.0 | 5.0 | 5.0 | 5.0 | 5.0 | 5.0 | 5.0 | 5.0 | 5.0 |
| Ammonia/HCl | | | | | Ad pH 9.5 | | | | |
| Water | | | | | Ad 100.0 | | | | |

The compositions from above are applied directly onto keratin fibers.

As an alternative, they can also be mixed with the following oxidative composition:

| | % by weight |
|---|---|
| Hydrogen peroxide | 6.0 |
| Phosphoric acid/NaOH | ad pH 3.0 |
| Etidronic acid | 0.05 |
| Water | ad 100.0 |

Suitable mixing ratios of the dyeing composition with the oxidative composition is in range of 0.1 to 10 by weight, preferably in the range of 0.5 to 3 by weight.

The invention claimed is:

1. A dyeing composition for keratin fibers, comprising:
one or more first direct dyes selected from HC Blue 18, HC Red 18, HC Yellow 16, and salts thereof;
one or more second direct dyes selected from Disperse Black 9, Acid Yellow 1, 2-amino-6-chloro-4-nitrophenol and salts thereof; and
one or more alkalizing agents.

2. The composition according to claim 1, wherein a weight ratio of the one or more first direct dyes to the one or more second direct dyes is in a range of 5 to 0.05.

3. The composition according to claim 1, wherein a total concentration of the one or more first direct dyes is in a range of 0.001% to 1% by weight calculated to the total weight of the composition.

4. The composition according to claim 1, wherein a total concentration of the one or more second direct dyes is in a range of 0.001% to 2% by weight, calculated to the total weight of the composition.

5. The composition according to claim 1, wherein the one or more alkalizing agents is selected from ammonia, organic alkalizing agents, and salts thereof.

6. The composition according to claim 1, wherein a total concentration of the one or more alkalizing agents is in a range of 0.1% to 40% by weight, calculated to the total weight of the composition.

7. The composition according to claim 1, wherein the composition is an aqueous composition having a pH in a range of 7 to 12.

8. The composition according to claim 1, wherein the composition is a liquid composition at 25° C. and atmospheric pressure, and wherein the composition further comprises one or more organic solvents and less than 1% by weight of water, calculated to the total weight of the composition.

9. The composition according to claim 1, wherein the composition is a powder composition and comprises one or more pulverulent excipients.

10. The composition according to claim 1, further comprising, one or more dye compounds different from the one or more first direct dyes and the one or more second direct dyes selected from oxidative dye precursors, oxidative dye couplers, and direct dyes.

11. A two-part hair dyeing composition, comprising:
a first composition according to claim 1; and
a second aqueous composition having a pH in a range of 1 to 6 and optionally comprising one or more oxidizing agents.

12. A method for dyeing keratin fibers, comprising:
providing the composition of claim 1 and optionally mixing with a second aqueous composition having a pH in a range of 1 to 6 and optionally comprising one or more oxidizing agents to yield a ready-to-use composition having a pH in a range of 7 to 12;
applying the ready-to-use composition onto the keratin fibers and leaving it for a time period in a range of 1 min to 60 min; and
optionally rinsing-off the keratin fibers and optionally drying the keratin fibers.

13. A method for dyeing keratin fibers, comprising:
applying a first aqueous composition onto the keratin fibers having a pH in a range of 7 to 12 and comprising one or more first direct dyes selected from HC Blue 18, HC Red 18, HC Yellow 16, and salts thereof, and one or more alkalizing agents;
leaving the first aqueous composition onto the keratin fibers for a time period in a range of 1 min to 60 min, and optionally rinsing-off the keratin fibers and optionally drying the keratin fibers;
applying a second aqueous composition onto the keratin fibers having a pH in a range of 3 to 12 and comprising one or more second direct dyes selected from Disperse Black 9, Acid Yellow 1, 2-amino-6-chloro-4-nitrophenol and salts thereof, and one or more alkalizing agents; and leaving the second aqueous composition onto the keratin fibers for a time period in a range of 1 min to 60 min, optionally rinsing-off the keratin fibers and optionally drying the keratin fibers.

14. The method according to claim 13, wherein the applying the second aqueous composition is performed without a time delay after the leaving the first aqueous composition, or with a delay of 1 to 5 washes of the keratin fibers.

15. A kit-of-parts for dyeing of keratin fibers, comprising:

a first composition comprising one or more first direct dyes selected from HC Blue 18, HC Red 18, HC Yellow 16, and salts thereof, and one or more alkalizing agents;

a second composition comprising one or more second direct dyes selected from Disperse Black 9, Acid Yellow 1, 2-amino-6-chloro-4-nitrophenol and salts thereof, and one or more alkalizing agents; and optionally an aqueous oxidizing composition having a pH in a range of 1 to 6.

16. The composition according to claim 1, wherein a weight ratio of first direct dyes to second direct dyes is in a range of 1.5 to 0.15.

17. The composition according to claim 1, wherein the one or more alkalizing agents is selected from organic alkyl, alkanol amines, and salts thereof according to the following general structure:

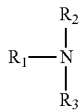

wherein R1, R2, and R3 are independently selected from H, linear C1-C6 alkyl which may be substituted with one hydroxyl group, or branched C3-C12 alkyl or alkanol, wherein at least one of R1, R2, or R3 is different from H.

* * * * *